United States Patent [19]

Quinlan

[11] Patent Number: 4,514,320

[45] Date of Patent: Apr. 30, 1985

[54] HALIDE FREE CORROSION INHIBITORS

[75] Inventor: Patrick M. Quinlan, Webster Groves, Mo.

[73] Assignee: Petrolite Corporation, St. Louis

[21] Appl. No.: 588,593

[22] Filed: Mar. 12, 1984

Related U.S. Application Data

[62] Division of Ser. No. 200,817, Oct. 27, 1980.

[51] Int. Cl.³ .............................................. C23F 11/14
[52] U.S. Cl. ..................................... 252/392; 252/390
[58] Field of Search ................................ 252/390, 392

[56] References Cited

U.S. PATENT DOCUMENTS

| | | | |
|---|---|---|---|
| 2,542,982 | 2/1951 | Bartleson et al. | 252/391 |
| 3,502,578 | 3/1970 | Ralfsnider | 252/391 |
| 3,668,137 | 6/1972 | Gardner | 252/391 |
| 3,775,320 | 11/1973 | Vigo et al. | 252/391 |
| 3,821,232 | 6/1974 | Redmore | 546/348 |
| 3,896,050 | 7/1975 | White | 252/391 |
| 3,940,248 | 2/1976 | Yamaguchi et al. | 252/391 |
| 3,981,869 | 9/1976 | Ziemak | 548/152 |
| 4,000,079 | 12/1976 | Rasp et al. | 548/152 |
| 4,022,785 | 5/1977 | Alink et al. | 546/348 |
| 4,046,895 | 9/1977 | Curran et al. | 546/108 |
| 4,071,746 | 1/1978 | Quinlan | 252/392 X |
| 4,106,904 | 8/1978 | Alink et al. | 252/392 |
| 4,188,359 | 2/1980 | Quinlan | 252/391 |
| 4,212,842 | 7/1980 | Hartke | 252/392 X |
| 4,263,167 | 4/1981 | Mago | 252/391 |

FOREIGN PATENT DOCUMENTS

| | | | |
|---|---|---|---|
| 595706 | 4/1960 | Canada | 548/146 |
| 631385 | 11/1961 | Canada | 546/348 |
| 1159453 | 12/1963 | Fed. Rep. of Germany | 548/146 |
| 1802639 | 5/1969 | Fed. Rep. of Germany | 546/108 |
| 1521790 | 3/1971 | Fed. Rep. of Germany | 252/391 |
| 740936 | 11/1955 | United Kingdom | 544/242 |
| 845486 | 8/1960 | United Kingdom | 544/242 |

*Primary Examiner*—Leland A. Sebastian
*Attorney, Agent, or Firm*—Sidney B. Ring; Leon Zitver

[57] ABSTRACT

This invention relates to non-halogen salts of nitrogen and/or nitrogen-sulfur heterocyclics as corrosion inhibitors for stainless steel-containing systems. These are more effective as corrosion inhibitors when employed in combination with surfactants, preferably of the nonionic type such as oxyalkylates.

4 Claims, No Drawings

HALIDE FREE CORROSION INHIBITORS

This is a division of application Ser. No. 200,817, filed Oct. 27, 1980, pending.

This invention relates to corrosion inhibitors such as those designed for use in acid cleaning solvents which are used in cleaning industrial high temperature boilers and steam generators. Because of the presence of stainless steel components in these boilers and generators, inhibitors which contain halides have to be avoided since halide contamination will cause stress-corrosion cracking in these components.

In the patent application Ser. No. 101,953 filed Dec. 10, 1979, N. S. Thompson, now U.S. Pat. No. 4,446,056, there is described and claimed nitrogen and/or sulfur-nitrogen heterocycles. While they are useful as corrosion inhibitors in mineral acids, they are not as suitable by themselves in the present system.

I have now discovered that when the compositions described in the above application are reacted with an acid, excluding halogen acids, they become more soluble in the acidic medium in which they are to be used.

I have further discovered that the effectiveness of the salts can further be enhanced by the presence of surfactants, particularly non-ionic surfactants such as oxyalkylated surfactants. The use of surfactants, in the compositions of this invention, not only enhances the overall corrosion inhibition, but also produces a composition of excellent solubility in the various acid cleaning solvents. In effect there is no "gunking out" of the inhibitor or residual film left on the cleaning surface after use.

Thus, this invention relates to acid corrosion inhibitor composition comprising:
(1) An acid salt(s) of nitrogen and/or sulfur-nitrogen heterocycles described in patent application Ser. No. 101,953
(2) A surfactant which is preferably an oxyalkylated surfactant.

Non-limiting examples of suitable acids that may be employed to form the salt(s) of this invention include: sulfuric, nitric, phosphoric, acetic, formic, hydroxyacetic, organic acids such as sulfonic acids, etc., and the like.

Any suitable surfactant can be employed. The surfactants which are most usually employed in the practice of this invention are oxyalkylated surfactants or more specifically polyalkylene ether or polyoxyalkylene surfactants. Oxyalkylated surfactants as a class are well known. The possible sub-classes and specific species are legion. The methods employed for the preparation of such oxyalkylated surfactants are also too well known to require much elaboration. Most of these surfactants contain, in at least one place in the molecule and often in several places, an alkanol or a polyglycolether chain. These are most commonly derived by reacting a starting molecule, possessing one or more oxyalkylatable reactive groups, with an alkylene oxide such as ethylene oxide, propylene oxide, butylene oxide, etc. However, they may be obtained by other methods such as shown in U.S. Pat. Nos. 2,588,771 and 2,596,091-3, or by esterification or amidification with an oxyalkylated material, etc. Mixtures of oxides may be used as well as successive additions of the same or different oxides may be employed. Any oxyalkylatable material may be employed. As typical starting materials may be mentioned alkyl phenols, phenolic resins, alcohols, glycols, amines, organic acids, carbohydrates, mercaptans, and partial esters of polybasic acids. In general, the art teaches that, if the starting material is water-soluble, it may be converted into an oil-soluble surfactant by the addition of polypropoxy or polybutoxy chains. If the starting material is oil-soluble, it may be converted into a water soluble product. Subsequent additions of ethoxy units to the water-soluble surfactant by the addition of polyethoxy chains tend to increase the water solubility, while, subsequent additions of high alkoxy chains tend to increase the oil solubility. In general, the final solubility and surfactant properties are a result of a balance between the oil-soluble and water-soluble portions of the molecule.

In the practice of this invention I have found that suitable surfactants may be prepared from a wide variety of starting materials. For instance, if I begin with an oil-soluble material such as a phenol or a long chain fatty alcohol and prepare a series of products by reaction with successive portions of ethylene oxide, I find that the members of the series are successively more water-soluble. Similarly it is possible to start with water or a water-soluble material such as polyethylene glycol and add, successively, portions of propylene oxide. The members of this series will be progressively less water-soluble and more oil-soluble. There will be a preferred range where the materials are useful for the practice of this invention.

In general, the compounds which would be selected are oxyalkylated surfactants of the general formula $$Z[(OA)_nOH]_m$$

wherein Z is the oxyalkylatable material, A is the radical derived from the alkylene oxide which can be, for example, ethylene, propylene, butylene, and the like, n is a number determined by the moles of alkylene oxide reacted, for example 1 to 2000 or more and m is a whole number determined by the number of reactive oxyalkylatable groups. Where only one group is oxyalkylatable as in the case of a monofunctional phenol or alcohol R'OH, then m=1. Where Z is water, or a glycol, m=2. Where Z is glycerol, m=3, etc.

In certain cases, it is advantageous to react alkylene oxides with the oxyalkylatable material in a random fashion so as to form a random copolymer on the oxyalkylene chain, i.e., the $[(OR)_nOH]_m$ chain such as —AAbAAABBABABBABBA—. In addition, the alkylene oxides can be reacted in an alternate fashion to form block copolymers on the chain, for example

—BBBAAABBBAAAABBBB— or

—BBBBAAACCCAAAABBBB— where A is the unit derived from one alkylene oxide, for example ethylene oxide, and B is the unit derived from a second alkylene oxide, for example propylene oxide, and C is the unit derived from a third alkylene oxide, for example, butylene oxide, etc. Thus, these compounds include terpolymers or higher copolymers polymerized randomly or in a blockwise fashion or many variations or sequential additions.

Thus, $(OR)_n$ in the above formula can be written —$A_aB_bC_c$— or any variation thereof, wherein a, b and c are 0 or a number provided that at least one of them is greater than 0.

It cannot be overemphasized that the nature of the oxyalkylatable starting material used in the preparation of the surfactant is not critical. Any species of such material can be employed. By proper additions of alkylene oxides, this starting material can be rendered suitable as a surfactant and its suitability can be evaluated by testing in the corrosion system.

| REPRESENTATIVE EXAMPLES OF Z | |
|---|---|
| No. | Z |
| 1 | $RC(=O)-O-$ |
| 2 | $R_n$-(phenyl)-$O-$ |
| 3 | $R-O-$ |
| 4 | $R-S-$ |
| 5 | $R-C(=O)-N-H$ |
| 6 | $R-C(=O)-N\langle$ |
| 7 | $R-N(H)-$ |
| 8 | $RN\langle$ |
| 9 | Phenol-aldehyde resins. |
| 10 | $-O-$ (Ex: Alkylene oxide block polymers). |
| 11 | $-O-$(phenyl-R)$-X-$(phenyl-R)$-O-$ ; $X = O, -S-, -CH_2-S(=O)_2-,$ etc. |
| 12 | $R-S-CH_2C(=O)-O-$ |
| 13 | $RPO_4H$ |
| 14 | $RPO_4=$ |
| 15 | $PO_4=$ |
| 16 | $R_n$-(cyclohexyl)-$SO_2N(H)-$ |
| 17 | $R_n$-(cyclohexyl)-$SO_2N=$ |
| 18 | $RC(=O)-N(H)-$(cyclohexyl)-$N$ |
| 19 | Polyol-derived (Ex: glycerol, glucose, pentaerithrytol). |
| 20 | Anhydrohexitan or anhydrohexide derived (Spans andd Tweens). |
| 21 | Polycarboxylic derived. |
| 22 | $-(CHCH_2-O)_n-$ with $CH_2$-amino side chain |

Examples of oxyalkylatable materials derived from the above radicals are legion and these, as well as other oxyalkylatable materials, are known to the art. A good source of such oxyalkylatable materials, as well as others, can be found in "Surface Active Agents and Detergents," vols. 1 and 2, by Schwarz et al., Interscience Publishers (vol. 1, 1949, vol. 2, 1958), and the patents and references referred to therein.

Non-limiting examples of the preparation of the nitrogen and/or nitrogen-sulfur heterocyclics and the acid salt(s) thereof are as follows.

EXAMPLE 1

To a suitable reactor is charged 300 cc of aqueous ammonia ($NH_4OH \sim 58\%$). Butyraldehyde (200 grams) is added at a rate such that the reaction mixture is maintained at 35°–45° C. Addition time is about 45 min. Stirring is continued for an additional 90 minutes and then the mixture is allowed to settle and separate into two phases. The upper organic phase was identified as 2,4,6-tripropyl 1,3,5-hexahydrotriazine, containing 1 mole of water.

Anal. calculated for $C_{12}H_{27}N_3 \cdot H_2O$: N, 18.2; Found 17.9.

The organic phase (200 grams) was charged to a 500 ml reactor equipped with stirrer, thermometer and off-gas condenser attached to a Dean Stark trap. Ammonium nitrate, 2 grams was added and the mixture heated gradually to 180° C. over a 4 hour period. During this period copious evolution of ammonia gas took place; low boiling products, mainly water, were removed during the reaction. The product (160 gm) was a clear amber liquid. The product was separated by preparative gas chromatography into two major components. These were identified as 2-propyl 3,5-diethyl pyridine and 1-butyl, 2-propyl, 3,5-diethyl 1,2-dihydropyridine.

EXAMPLE 2

To 100 grams of 2,4,6-tripropyl 1,3,5-hexahydrotriazine prepared as described in Example 1, was added 1.5 grams ammonium nitrate and 1.0 gram sulfur. The mixture was heated as described in Example 1 and the resulting product was a clear amber stench liquid. Analysis showed incorporation of 90% of the sulfur added.

Using the reactants and procedure of Example 2 except for the following % of sulfur and/or sulfur-containing reactant, the following sulfur-containing compositions were prepared. The results are summarized in Table 1.

TABLE 1

| Example No. | Sulfur Compound | Wgt. of Sulfur-containing Reactant | % Sulfur of wgt. of Reactants |
|---|---|---|---|
| 3 | sulfur | 5 | 5 |
| 4 | sulfur | 10 | 10 |
| 5 | sulfur | 20 | 20 |

EXAMPLE 6

To a cooled aqueous 28% ammonia solution (300 cc) and sulfur (10 grams) was added 200 grams butyraldehyde at such a rate that a temperature of ≦35° C. was maintained. The mixture was stirred for 24 hours and the resulting layers were separated, in an upper organic phase and lower aqueous phase. The organic phase was charged to a reactor equipped with stirrer, thermometer, and an off-gas condenser attached to a Dean Stark trap. Ammonium nitrate, 2 grams, was added and the mixture heated gradually to 180° C. over a period of 4 hours. During this period copious evolution of ammonia gas took place; low boiling products, mainly water, were removed during the reaction. The resulting product was a clear amber stench liquid. Analysis indicated ≧90% of sulfur charged present in the product.

As described in example 6, the following sulfur-containing compositions were prepared. The details are summarized in Table 2.

TABLE 2

| Example No. | Sulfur Compound | Wt. Sulfur Compound | % Sulfur of Wgt. of Reactants |
|---|---|---|---|
| 7 | sulfur | 1.0 g | 0.5 |
| 8 | sulfur | 5.0 g | 2.5 |
| 9 | sulfur | 20.0 g | 10.0 |

EXAMPLE 10

Place in a pressure reactor, a mixture of 200 grams cyclohexanone and 10 grams ammonium nitrate. Add with stirring ammonia gas and maintain a pressure of 30–40 psi while keeping the reaction temperature between 50°–60° C. Continue stirring for 10–24 hours or until the reaction shows no sign of taking up more ammonia. When the reaction is over the stirrer is turned off and the mass upon settling separates into two layers. The lower viscous organic which is identified as 2,2,4,4-dipentamethylene 5,6-tetramethylene 2,2,4,5-tetrahydropyrimidine is charged to a 500 ml reactor equipped with stirrer, thermometer and an off-gas condenser attached to a Dean Stark trap. Carefully add 4 grams nitric acid or 10 grams ammonium nitrate and heat the mixture gradually to 190°–200° C. for 5–6 hours while removing any water or low boiling distillate. Evolution of ammonia gas commences at about 110°–120° C. and is very strong at 150° C. The progress and completion of the reaction can be followed by the decrease in the off-gas evolution and by the change in the infrared spectral characteristics, the peak at 6.02μ, —C=N, disappears and a strong new peak at 6.4μ (pyridine) appears. The final product (175 grams) is a dark, very viscous liquid and is identified as 9-pentyl 1,2,3,4,5,6,7,8-octahydrophenanthridine).

EXAMPLE 11

To 100 grams of the intermediate pyrimidine prepared as described in Example 10 was added 10 grams sulfur and 5 grams ammonium nitrate and the mixture heated gradually to 190°–200° C. for 6 hours. The resulting product was a dark, very viscous stench liquid. Analysis showed ≧85% of sulfur charged present in the final product.

EXAMPLE 12

Same as Example 11 except 5.0 grams sulfur was added.

EXAMPLE 13

Same as Example 11 except 1.0 gram sulfur was added.

EXAMPLE 14

Place in a pressure reactor a mixture of 200 grams cyclohexanone, 10 grams sulfur and 10 grams ammonium nitrate. Add with stirring ammonia gas and maintain a pressure of 30–40 psi while keeping the reaction temperature between 50°–60° C. This reaction is exothermic and some cooling might be required. Continue stirring for 10–20 hours. When the reaction is over, the stirrer is turned off and the mass upon settling separates into two layers. The lower organic layer (205 grams) is drawn off and charged to a 500 ml reactor equipped with stirrer, thermometer and a Dean Stark trap attached to a reflux condenser. Carefully add 4 grams nitric acid or 10 grams ammonium nitrate and heat the mixture gradually to 190°–200° C. for 6 hours. The resulting product is a dark, viscous stench liquid. Gas chromatography shows the product to consist mainly of two components, phenanthridine and 2,2-pentamethylene 4,5-tetramethylene 3-thiazoline. Analysis showed ≧85% of sulfur charged present in the final product.

EXAMPLE 15

Same as Example 14, except 20 grams sulfur was added. This product was a semi-solid.

EXAMPLE 16

Same as Example 14, except 5 grams sulfur was added.

EXAMPLE 17

Same as Example 14, except 2 grams sulfur was added.

TABLE 3

| Example No. | Sulfur Compound | Wt. Sulfur Compound | % Sulfur of Wgt. of Reactants |
|---|---|---|---|
| 18 | — | — | — |
| 19 | sulfur | 10 | 10 |
| 20 | " | 5 | 5 |
| 21 | " | 1 | 1 |
| 22 | " | 10 | 5 |
| 23 | " | 20 | 10 |
| 24 | " | 5 | 2.5 |
| 25 | " | 2 | 1.0 |

The sulfur-containing heterocyclic products are primarily thiazoles and thiazolines characterized by the presence of the following moieties:

(1) Thiazole

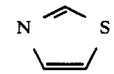

(2) Thiazoline

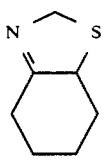

and substituted derivatives thereof, for example

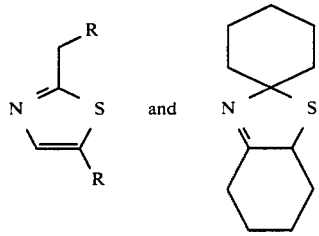

where R is the R moiety of the aldehyde or ketone reacted.

The following is an outline of the reactions occurring in the above examples.

EXAMPLE 1

Equation 1

$$3 \text{ RCHO} + \text{NH}_3(\text{NH}_4\text{OH}) \longrightarrow$$

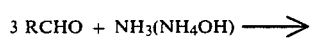

2,4,6-trialkyl 1,3,5-hexahydrotriazine

Eq. 2

$$\longrightarrow \text{R.xH}_2\text{O} \longrightarrow$$

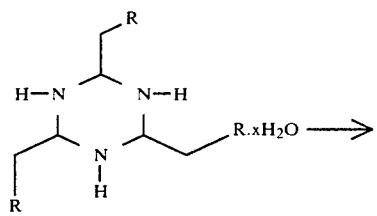

alkylpyridine

N—alkyldihydro-pyridine

EXAMPLES 2-5

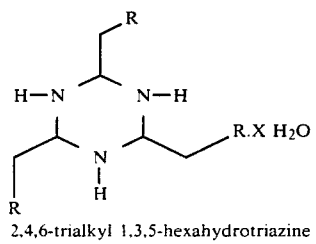

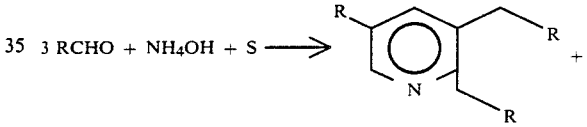

alkylpyridine     N—alkyldihydropyridine

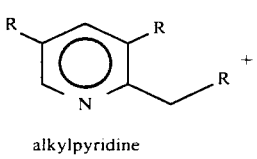

2-Propyl-5 ethyl thiazole

EXAMPLES 6-9

$$3 \text{ RCHO} + \text{NH}_4\text{OH} + \text{S} \longrightarrow$$

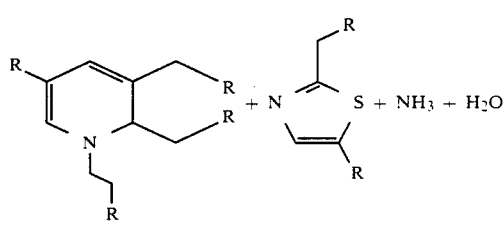

alkylpyridine

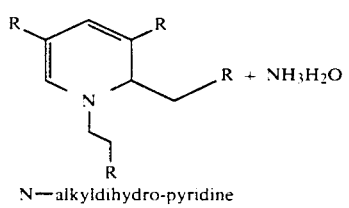

N—alkyldihydropyridine

2-Propyl-5 ethyl thiazole

EXAMPLE 10

Eq. 1

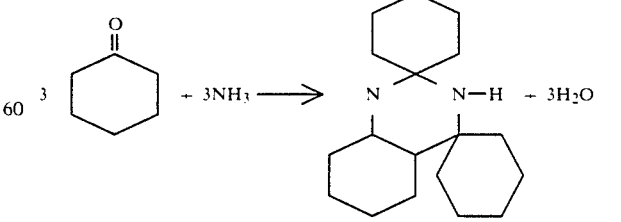

*Product a
*2,2,4,4-dipentamethylene 5,6-tetramethylene 2,2,4,4-tetrahydropyrimidine -continued Product a $\xrightarrow[\Delta]{Cat.}$ [structure] + NH₃   Eq. 2

*Product b
*9-pentyl 1,2,3,4,5,6,7,8-octahydrophenanthridine

EXAMPLES 11–13

[structure] NH + xS $\xrightarrow[\Delta]{Cat.}$

[structure] Phenanthridine + N S + NH₃

2,2-pentamethylene
4,5-tetramethylene
3-thiazoline

EXAMPLES 14–17

[structure] + NH₃ + xS ⟶

[structure] + N S + NH₃

The following examples illustrate the preparation of the corrosion inhibitor compositions of this invention.

EXAMPLE 26

To 50 g. of the reaction products of Example 3 dissolved in 35 g. of 2-propanol and 35 g. of water was slowly added, with cooling and stirring, 20 g. of concentrated sulfuric acid. The product was a clear, bright liquid. To this liquid was added 20 g. of nonyl phenol that had been condensed with 15 mols of ethylene oxide.

EXAMPLE 27

To 50 g. of the reaction products of Example 4 dissolved in 33.5 g. of 2-propanol and 33.5 g. of water was slowly added, with cooling and stirring, 17 g. of 70% nitric acid. The product was a clear, bright liquid. To this liquid was added 17 g. of nonyl phenol that had been condensed with 15 mols of ethylene oxide.

EXAMPLE 28

To 50 g. of the reaction products of Example 2 dissolved in 40 g. of 2-propanol and 22 g. of water was slowly added, with cooling and stirring, 12 g. of 85% phosphoric acid. To the resulting liquid was added 13 g. of hexadecyl amine that had been condensed with 23 mols of ethylene oxide.

EXAMPLE 29

To 54 g. of the reaction products of Example 12 dissolved in 37 g. of 2-propanol and 37 g. of water was slowly added, with cooling and stirring, 20 g. of concentrated sulfuric acid. To the resulting liquid was added 13 g. of nonyl phenol that had been condensed with 15 mols. of ethylene oxide.

In a similar manner the following corrosion inhibitor compositions were prepared.

EXAMPLE 30

| | |
|---|---|
| Products of Ex. 12 | 54 g. |
| Nitric acid (70%) | 17 g. |
| Dinonyl phenol condensed with 17 mols ethylene oxide | 13 g. |
| 2-propanol | 35.5 g. |
| Water | 35.5 g. |

EXAMPLE 31

| | |
|---|---|
| Products of Ex. 14 | 54 g. |
| Sulfuric acid (conc.) | 20 g. |
| Nonyl phenol condensed with 15 mols ethylene oxide | 14 g. |
| 2-propanol | 37 g. |
| Water | 37 g. |

EXAMPLE 32

| | |
|---|---|
| Products of Ex. 10 | 54 g. |
| Nitric acid (70%) | 17 g. |
| Nonyl phenol condensed with 10 mols ethylene oxide | 14 g. |
| 2-propanol | 35.5 g. |
| Water | 35.5 g. |

EXAMPLE 33

| | |
|---|---|
| Products of Ex. 12 | 54 g. |
| Phosphoric acid (85%) | 12 g. |
| nonyl phenol condensed with 15 mols ethylene oxide | 13 g. |
| 2-propanol | 66 g. |

EXAMPLE 34

| | |
|---|---|
| Products of Ex. 11 | 54 g. |
| Glacial acetic acid | 17 g. |
| oleyl amine condensed with 22 mols ethylene oxide | 14 g. |
| 2-propanol | 35.5 g. |
| Water | 35.5 g. |

EXAMPLE 35

| | |
|---|---|
| Products of Ex. 19 | 52 g. |
| Sulfuric acid (conc.) | 19 g. |
| nonyl phenol condensed with 15 moles ethylene oxide | 12 g. |
| 2-propanol | 35.5 g. |
| Water | 35.5 g. |

The following tests were conducted to demonstrate the increased effectiveness of the acid cleaning inhibitor compositions of this invention over the nitrogen and sulfur-nitrogen and heterocycles described in patent application Ser. No. 101,953.

TABLE I

| | |
|---|---|
| Temperature | 175° F. |
| Duration of test | 6 hours |
| Corrodent | 8% Formic Acid |
| Inhibitor Concentration | 0.2% |
| Coupons | AISI 1020 mild steel |
| Volume/Surface ratio | 25 ml/sq. in. |
| Product of Example | Corrosion rate (lbs./ft$^2$/24 hrs.) |
| 3 (Composition of S.N. 101,953) | 0.009 |
| 20 (Composition of S.N. 101,953) | 0.010 |
| 26 (Composition of this invention) | 0.0035 |
| 31 (Composition of this invention) | 0.0020 |
| Blank | 0.070 |

The following tests results illustrate the effectiveness of the compositions of this invention as corrosion inhibitors in acid cleaning solvents. The test procedure utilized was the same as before.

TABLE II

| | |
|---|---|
| Temperature | 200° F. |
| Duration of test | 16 hours |
| Corrodent | 4% Hydroxyacetic acid and 2% Formic acid mixture |
| Inhibitor concentration | 0.2% |
| Coupons | AISI 1020 mild steel |
| Volume/Surface ratio | 25 ml./sq. in. |
| Product of Example | Corrosion rate (lbs./ft$^2$/24 hrs.) |
| 26 | 0.0075 |
| 27 | 0.0070 |
| 29 | 0.0027 |
| 30 | 0.0027 |
| 33 | 0.0031 |
| Blank | 0.065 |

TABLE III

| | |
|---|---|
| Temperature | 175° F. |
| Duration of test | 6 hours |
| Corrodent | 10% formic acid |
| Inhibitor concentration | 0.2% |
| Coupons | AISI 1020 mild steel |
| Volume/Surface ratio | 25 ml./sq. in. |
| Product of Example | Corrosion rate (lbs./ft$^2$/24 hrs.) |
| 27 | 0.0085 |
| 28 | 0.0076 |
| 30 | 0.0020 |
| 31 | 0.0022 |
| 32 | 0.0023 |
| Blank | 0.060 |

I claim:

1. A corrosion inhibiting composition comprising non-halogen salts of alkylpyridines and N-alkyldihydropyridines, said composition also containing an effectiveness enhancing amount of an oxyalkylate surfactant.

2. The composition of claim 1 where the compositions are 2-propyl 3,5 diethyl pyridine and 1-butyl, 2-propyl 3,5-diethyl 1,2-dihydropyridine.

3. A process of inhibiting corrosion in a system containing stainless steel which comprises treating such system with the composition of claim 1.

4. A process of inhibiting corrosion in a system containing stainless steel which comprises treating such system with the composition of claim 2.

* * * * *